United States Patent [19]
Malice, Jr. et al.

[11] Patent Number: 6,162,250
[45] Date of Patent: Dec. 19, 2000

[54] SELF-FORMING PARTIAL BREAST PROSTHESIS WITH ENCAPSULATED CATALYST AND A METHOD OF MAKING THE SAME

[75] Inventors: Louis F. Malice, Jr., Marietta, Ga.; Robert James Halley, Loveland, Colo.

[73] Assignee: Coloplast Corporation, Marietta, Ga.

[21] Appl. No.: 09/267,319

[22] Filed: Mar. 12, 1999

Related U.S. Application Data

[60] Provisional application No. 60/077,728, Mar. 12, 1998.
[51] Int. Cl.$^7$ .................................................... A61F 2/52
[52] U.S. Cl. ................................ 623/7; 264/222; 128/898
[58] Field of Search ........................... 623/7, 8; 128/898; 264/222

[56] References Cited

U.S. PATENT DOCUMENTS

| | | |
|---|---|---|
| 4,100,627 | 7/1978 | Brill, III . |
| 4,317,241 | 3/1982 | Knoche ........................................ 3/36 |
| 4,401,492 | 8/1983 | Pfommer . |
| 4,665,148 | 5/1987 | Wong . |
| 4,755,588 | 7/1988 | Vallance et al. . |
| 4,787,905 | 11/1988 | Loi . |
| 4,790,848 | 12/1988 | Cronin ........................................ 623/8 |
| 5,067,967 | 11/1991 | Ersek et al. . |
| 5,071,433 | 12/1991 | Naestoft et al. . |
| 5,258,036 | 11/1993 | Edenbaum et al. ........................ 623/33 |
| 5,352,307 | 10/1994 | Wild . |
| 5,370,688 | 12/1994 | Schulz et al. . |
| 5,407,445 | 4/1995 | Tautvydas et al. ......................... 623/8 |
| 5,411,554 | 5/1995 | Scopelianos et al. ...................... 623/8 |
| 5,534,609 | 7/1996 | Lewis et al. .............................. 528/15 |
| 5,658,329 | 8/1997 | Purkait ..................................... 623/11 |
| 5,713,960 | 2/1998 | Christensen et al. ..................... 623/11 |
| 5,738,812 | 4/1998 | Wild ....................................... 264/102 |
| 5,741,877 | 4/1998 | Tiffany .................................... 528/15 |
| 5,824,075 | 10/1998 | Thielbar ................................... 623/7 |
| 5,888,231 | 3/1999 | Sandvig et al. .......................... 623/36 |
| 5,902,335 | 5/1999 | Snyder, Jr. ................................ 623/7 |
| 5,941,909 | 8/1999 | Purkait .................................... 623/11 |

FOREIGN PATENT DOCUMENTS

WO 99/45862  9/1999  WIPO .

*Primary Examiner*—David H. Willse
*Assistant Examiner*—Suzette J. Jackson
*Attorney, Agent, or Firm*—Needle & Rosenberg P.C.

[57] ABSTRACT

The present invention is directed to a self-forming partial breast prosthesis suitable for use with partial mastectomies. The present invention is further directed to a method of making the self-forming partial breast prosthesis.

38 Claims, No Drawings

SELF-FORMING PARTIAL BREAST PROSTHESIS WITH ENCAPSULATED CATALYST AND A METHOD OF MAKING THE SAME

This application claims benefit of Provisional Application 60/077,728 filed Mar. 12, 1998.

FIELD OF THE INVENTION

The present invention is directed to a self-forming partial breast prosthesis suitable for use with partial mastectomies. The present invention is further directed to a method of making the self-forming partial breast prosthesis.

BACKGROUND OF THE INVENTION

In the event of breast cancer, surgeons often perform mastectomies in order to remove all or part of the cancerous breast. In recent years, surgeons have increasingly utilized partial mastectomies, such as lumpectomies and quadrectomies, when they are sufficient to remove the cancerous tissue from the breast.

In cases involving complete mastectomies, patients can choose from a wide variety of prosthetic devices in order to provide a symmetrical appearance under clothing. Patients who undergo partial mastectomies are presently able to choose a partial prosthesis. Presently, partial breast prostheses are offered in a few different shapes, which each come in a few different sizes. The patient must select an off-the-shelf partial prosthesis having a shape and size that provides the patient with the most symmetry under clothing.

In many cases, the off-the-shelf partial prosthesis have shapes and sizes, which do not provide a good fit with the remaining portion of the patient's breast. Therefore, there exists a need in the art for a partial prosthesis that can be custom tailored to the size and shape of the patient's breast.

SUMMARY OF THE INVENTION

The present invention provides a self-forming partial breast prosthesis suitable for use with partial mastectomies. The partial prosthesis includes a bag formed from two sheets of a thin film material. A catalyst is enclosed in a capsule formed from an inert material and placed within the bag. The bag is filled with a liquid that will cure at room temperature after it is mixed with the catalyst. When the prosthesis is ready to be fitted, the capsule is broken and the catalyst is mixed with the liquid. The prosthesis is then placed in the patient's bra and cures in the shape of the "mold" formed by the patient's breast and bra.

The various aspects of the present invention may be more clearly understood and appreciated from a review of the following detailed description of the disclosed embodiments.

DETAILED DESCRIPTION OF THE INVENTION

The present invention provides a self-forming partial breast prosthesis that conforms to a specific wearer's breast, a portion of which having been removed during a partial mastectomy procedure. The self-forming partial breast prosthesis of the present invention allows a mastectomy patient to choose an uncured, conformable prosthesis precursor, which may be easily transformed into a cured, prosthesis having a shape, which conforms to the patient's body and provides comfort and satisfaction to the patient.

The self-forming partial breast prosthesis of the present invention is formed from a partial breast prosthesis precursor. The partial breast prosthesis precursor comprises a bag, which contains a curable material, a capsule, and a catalyst within the capsule. The bag may be formed from a thin film material having a desired appearance and texture. The bag may comprise a variety of materials including, but not limited to, polyurethane and silicone polymers. Desirably, the bag material comprises one or more layers of a thin polyurethane film, which has a matte finish on the cup side. The edges of the bag are heat sealed to form a shape having a desired volume. The film material used to form the bag desirably has a film thickness of up to about 5 mils. More desirably, the film material has a film thickness of from about 1 mil to about 3 mils. Even more desirably, the film material has a film thickness of about 2.5 mils.

The bag is filled with an uncured material, which may be cured to form a hardened material having a desired amount of softness and texture. Suitable curable materials include, but are not limited to, silicone gels and silicone gel systems, which cure at room temperature with the aid of at least one catalyst. The choice of a particular curable material may be made by one of ordinary skill in the art given a patient's particular needs (i.e., degree of softness, etc.). Suitable curable materials are well known in the art of making external breast prosthesis, and any one may be used in the present invention. Suitable curable materials are disclosed in numerous publications including, but not limited to, U.S. Pat. Nos. 5,534,609 and 5,741,877, both of which are incorporated by reference.

In one embodiment of the present invention, the curable material comprises a polydimethylsiloxane (CAS Reg. No. 63148-62-9), a vinyldimethylsiloxy terminated polydimethylsiloxane (CAS Reg. No. 68951-99-5), and a methylhydrosiloxane-dimethylsiloxane copolymer (CAS Reg. No. 68037-59-2). In addition to the curable material, other materials may be combined with the curable material. Other additives include, but are not limited to, silicone oil, colorants, viscosity modifiers, cure inhibitors, cure accelerators, and fillers. Once the bag is filled with the curable material and optional additives, one or more capsules are inserted into the bag. It should be noted that the order of insertion of materials into the bag is not important. In other words, capsules may be placed in the bag prior to of after the curable material.

The capsule may be formed from any material, which provides a temporary enclosure for a catalyst material. Suitable materials for forming the capsule include, but are not limited to, polyethylene film. Desirably, the capsule is formed from a low molecular weight polyethylene film, PARAFILM™, available from Van Waters & Rogers (Kirkland, Wash.). In one embodiment of the present invention, a capsule is formed from PARAFILM™ by forming an envelope and heat sealing the edges with pressure.

The catalyst material may be any catalyst material, which initiates the curing process of the curable material. Suitable catalyst materials include, but are not limited to, platinum-containing catalysts. Suitable platinum-containing catalysts are disclosed in numerous publications including, but not limited to, U.S. Pat. Nos. 5,534,609 and 5,741,877, both of which are incorporated by reference. Desirably, the catalyst material comprises a water-soluble platinum-silicone complex. Such catalysts are available from a number of sources including, but not limited to, Catalyst VCAT RT (Witco Chemical), Catalyst PTS C OL (Wacker-Chemie GmbH; Germany), and Catalyst PC085 (United Chemical Technologies). The amount of catalyst may vary depending upon the desired rate of cure and the curable material.

Desirably, the amount of catalyst is up to about 3 wt % based on the total weight of catalyst and curable material. More desirably, the amount of catalyst is from about 0.5 wt % to about 1.0 wt % based on the total weight of catalyst and curable material. In addition to the catalyst material, one or more additional materials may be combined with the catalyst. Suitable additional materials include, but are not limited to, the above-mentioned additives. Once the curable material, capsule, and other additives are positioned within the bag, the fill port of the bag is heat sealed.

In one embodiment of the present invention, a self-forming partial breast prosthesis is formed from an outer bag of polyurethane and a curable silicone mixture comprising one or more polydimethylsiloxanes (CAS Reg. No. 63148-62-9) and one or more silicone vinyl polymers or vinyldimethylsiloxy terminated polydimethylsiloxanes (CAS Reg. No. 68951-99-5) in combination with one or more silicone hydride polymers or methylhydrosiloxane-dimethylsiloxane copolymers (CAS Reg. No. 68037-59-2). Desirably, the polydimethylsiloxane has a viscosity of from about 100 cSt to about 10,000 cSt. More desirably, the polydimethylsiloxane has a viscosity of from about 100 cSt to about 1,000 cSt. Even more desirably, the polydimethylsiloxane has a viscosity of from about 100 cSt to about 200 cSt. Desirably, the vinyldimethylsiloxy terminated polydimethylsiloxane has a viscosity of from about 1,000 cSt to about 165,000 cSt. More desirably, the vinyldimethylsiloxy terminated polydimethylsiloxane has a viscosity of from about 2,000 cSt to about 100,000 cSt. Even more desirably, the vinyldimethylsiloxy terminated polydimethylsiloxane has a viscosity of from about 2,000 cSt to about 65,000 cSt. Desirably, the methylhydrosiloxane-dimethylsiloxane copolymer has a viscosity of from about 5 cSt to about 1,000 cSt and a hydride content of from about 0.5 to about 5.0 mmol/g. More desirably, the methylhydrosiloxane-dimethylsiloxane copolymer has a viscosity of from about 10 cSt to about 100 cSt and a hydride content of from about 0.5 to about 2.0 mmol/g. Even more desirably, the methylhydrosiloxane-dimethylsiloxane copolymer has a viscosity of from about 40 cSt to about 50 cSt and a hydride content of from about 1.5 to about 2.0 mmol/g.

The present invention is further directed to a process of forming a self-forming partial breast prosthesis. The process may be used to form a variety of custom partial breast prosthesis having a desired size, color, and softness, while providing substantially complete conformity to the wearer's breast profile. In one embodiment of the present invention, a partial breast prosthesis precursor is produced as described above, wherein the precursor comprises an uncured liquid silicone formulation and a capsule containing a catalyst, both of which are enveloped by a durable polyurethane bag. The capsule within the bag is broken so that the contents of the capsule may be intermixed with the curable material. Desirably, the resulting mixture is mixed for about 5 to 10 minutes by kneading the bag. The precursor is then placed within a bra, next to a patient's partial breast. The precursor is allowed to cure for about 15 minutes. The resulting partial breast prosthesis conforms to the patient's breast profile.

In a further embodiment of the present invention, a variety of attachment systems, such as hook-and-loop fasteners, are easily adhered to the bag material to provide a durable and reliable means of attaching the prosthesis to the chest wall if desired. Suitable attachment systems include, but are not limited to, those disclosed in U.S. Pat. Nos. 5,071,433 to Naestoft et al. and 5,352,307 to Wild, both of which are incorporated by reference in their entirety.

In yet a further embodiment of the present invention, two layers of polyurethane film are heat sealed together to form an oval bag with an inlet on one end of the oval bag. A small capsule of platinum catalyst is placed into the bag. A mixture of silicone materials are injected into the bag. The mixture is formulated to cure at room temperature when mixed with the platinum catalyst. Entrapped air is removed from the bag, and the inlet is heat sealed. A patient is fitted with a prostheses precursor having the proper size and shape to match the patient's needs. The capsule of catalyst is broken open and the bag is kneaded for approximately 5–10 minutes in order to thoroughly mix the catalyst into the silicone mixture. The bag is then placed in the patient's bra in the position in which it will be worn. After approximately 15 minutes, the liquid cures into a silicone gel. It should be noted that mix time and cure time may vary depending on the curable material used, the catalyst, the size of the prosthesis, and other factors.

In a further embodiment of the present invention, a two-layer breast prosthesis may be formed, wherein the front or outermost layer of the breast prosthesis comprises a pre-cured prosthesis and the back or body-side layer comprises the self-forming breast prosthesis of the present invention. The pre-cured prosthesis provides preformed breast components such as a nipple, while the self-forming portion provides conformability and comfort to the wearer's chest.

The present invention is further described by the examples which follow. Such examples, however, are not to be construed as limiting in any way either the spirit or the scope of the present invention. In the examples, all chemical components are given in parts by weight, unless stated otherwise.

EXAMPLE 1

A self-forming partial breast prosthesis was formed using the following procedure. A bag was formed by heat sealing two sheets of polyurethane film having a thickness of 2.5 mils. at a temperature of about 385° C. and a pressure of about 25 bar for about 2 seconds. A curable material was formed by mixing the following components:

| | |
|---|---|
| Polydimethylsiloxane having a viscosity of 100 cSt | 350 g |
| Vinyldimethylsiloxy terminated polydimethylsiloxane having a viscosity of 2,000 cSt | 105 g |
| Vinyldimethylsiloxy terminated polydimethylsiloxane having a viscosity of 65,000 cSt | 45 g |
| Methylhydrosiloxane-dimethylsiloxane copolymer having a viscosity of 45 cSt | 4 g |

The curable composition was mixed and degassed.

A catalyst mixture was formed using the following components:

| | |
|---|---|
| Catalyst VCAT RT (available from Witco) | 1 g |
| Polydimethylsiloxane having a viscosity of 100 cSt | 49 g |

The catalyst mixture was sealed in a small capsule having dimensions of about ¼" diameter and 1" length. The capsule was formed by folding a low molecular weight polyethylene film, PARAFILM™ (available from Van Waters & Rogers), into an envelope and heat sealing the edges of the envelope under pressure.

The capsule and about curable composition were inserted into the bag through a fill port. The fill port was heat sealed to form a partial breast prosthesis precursor. The precursor was squeezed to break the capsule. The contents of the precursor were kneaded for about 5 to 10 minutes. The precursor was placed in a cradle and allowed to cure for about 15 minutes. The self-forming partial breast prosthesis conformed to the shape of the cradle.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of making a partial breast prosthesis comprising:
    forming a prosthesis precursor;
    positioning the precursor next to a patient's partial breast; and
    curing the precursor to form the partial breast prosthesis; wherein the partial breast prosthesis substantially conforms to the contour of the patient's partial breast.

2. The method of claim 1, wherein the prosthesis precursor comprises a bag containing a curable material and a capsule, wherein the capsule encloses a catalyst.

3. The method of claim 2, wherein the bag comprises a polyurethane film material.

4. The method of claim 2, wherein the curable material comprises one or more silicone polymers.

5. The method of claim 2, wherein the catalyst comprises a platinum-containing catalyst.

6. The method of claim 1, further comprising positioning the precursor between the patient's partial breast and the patient's bra.

7. A partial breast prosthesis formed by a method comprising:
    forming a prosthesis precursor;
    positioning the precursor next to a patient's partial breast; and
    curing the precursor to form the partial breast prosthesis; wherein the partial breast prosthesis substantially conforms to the contour of the patient's partial breast.

8. A partial breast prosthesis precursor comprising:
    a bag formed from a polymeric film material;
    a curable material within the bag;
    a capsule within the bag; and
    a catalyst enclosed by the capsule.

9. The partial breast prosthesis precursor of claim 8, wherein the polymeric film material comprises a polyurethane film.

10. The partial breast prosthesis precursor of claim 8, wherein the polymeric film material has a film thickness of up to about 5 mil.

11. The partial breast prosthesis precursor of claim 8, wherein the curable material comprises one or more silicone polymers.

12. The partial breast prosthesis precursor of claim 8, wherein the catalyst comprises a platinum-containing catalyst.

13. A partial breast prosthesis formed by curing the partial breast prosthesis precursor of claim 8.

14. A cured partial breast prosthesis comprising:
    an outer shell of polymeric film; and
    a cured gel material and a broken capsule enclosed by the outer shell.

15. A cured partial breast prosthesis comprising an outer shell of polymeric film and a cured gel material enclosed by the outer shell; wherein the cured partial breast prosthesis substantially conforms to a patient's partial breast and is formed by a method comprising:
    forming a prosthesis precursor;
    positioning the precursor next to a patient's partial breast; and
    curing the precursor to form the partial breast prosthesis.

16. The cured partial breast prosthesis of claim 13, further comprising a broken capsule within the outer shell.

17. The cured partial breast prosthesis of claim 13, wherein the cured gel material comprises a product resulting from the curing of one or more silicone polymers.

18. The method of claim 4, wherein the one or more silicone polymers comprises one or more polydimethylsiloxanes, vinyldimethylsiloxy terminated polydimethylsiloxanes, methylhydrosiloxane-dimethylsiloxane copolymers, or a combination thereof.

19. The partial breast prosthesis precursor of claim 11, wherein the one or more silicone polymers comprises one or more polydimethylsiloxanes, vinyldimethylsiloxy terminated polydimethylsiloxanes, methylhydrosiloxane-dimethylsiloxane copolymers, or a combination thereof.

20. The cured partial breast prosthesis of claim 17, wherein the one or more silicone polymers comprises one or more polydimethylsiloxanes, vinyldimethylsiloxy terminated polydimethylsiloxanes, methylhydrosiloxane-dimethylsiloxane copolymers, or a combination thereof.

21. The method of claim 1, further comprising adhering one or more attachment means to a surface of the prosthetic precursor.

22. The method of claim 21, wherein the attachment means comprises hook-and-loop fasteners.

23. The method of claim 1, wherein the step of forming the prosthetic precursor comprises:
    forming a bag having at least one opening;
    inserting a capsule into the at least one opening; and
    heat sealing the at least one opening.

24. The method of claim 23, wherein the step of forming the bag comprises:
    positioning a first film having a first peripheral edge adjacent to a second film having a second peripheral edge; and
    heat sealing the first peripheral edge of the first film to the second peripheral edge of the second film.

25. The method of claim 23, further comprising inserting a curable material into the at least one opening prior to heat sealing the at least one opening.

26. The partial breast prosthesis precursor of claim 8, wherein the polymeric film material comprises a polyurethane film; the curable material comprises one or more silicone polymers selected from polydimethylsiloxanes, vinyldimethylsiloxy terminated polydimethylsiloxanes, and methylhydrosiloxane-dimethylsiloxane copolymers; and the catalyst comprises a platinum-containing catalyst.

27. The partial breast prosthesis precursor of claim 8, further comprising one or more attachment means.

28. The partial breast prosthesis precursor of claim 27, wherein the attachment means comprises hook-and-loop fasteners.

29. The cured partial breast prosthesis of claim 14, wherein the polymeric film comprises a polyurethane film; and the cured gel material comprises one or more cured silicone polymers selected from polydimethylsiloxanes, vinyldimethylsiloxy terminated polydimethylsiloxanes, and methylhydrosiloxane-dimethylsiloxane copolymers.

30. The cured partial breast prosthesis of claim 14, further comprising one or more attachment means.

31. The cured partial breast prosthesis of claim 30, wherein the attachment means comprises hook-and-loop fasteners.

32. The method of claim 1, further comprising attaching an outermost pre-cured prosthetic layer to the prosthesis precursor.

33. The method of claim 32, wherein the outermost pre-cured prosthetic layer comprises one or more preformed breast components.

34. The partial breast prosthesis precursor of claim 8, further comprising an outermost pre-cured prosthetic layer attached to the bag.

35. The partial breast prosthesis precursor of claim 34, wherein the outermost pre-cured prosthetic layer comprises one or more preformed breast components.

36. The cured partial breast prosthesis of claim 14, wherein the cured partial breast prosthesis substantially conforms to a patient's partial breast.

37. The cured partial breast prosthesis of claim 14, further comprising an outermost pre-cured prosthetic layer attached to a surface of the outer shell.

38. The cured partial breast prosthesis of claim 37, wherein the outermost pre-cured prosthetic layer comprises one or more preformed breast components.

\* \* \* \* \*